United States Patent
Dorso et al.

(10) Patent No.: US 6,221,859 B1
(45) Date of Patent: Apr. 24, 2001

(54) CARBAPENEM ANTIBACTERIAL COMPOSITIONS AND METHODS OF THE TREATMENT

(75) Inventors: Karen L. Dorso, Franklin Park; Jesse J. Jackson, Howell; Charles J. Gill, Beachwood; Joyce Kohler, Woodbridge; Lynn L. Silver, Westfield, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/387,709

(22) Filed: Aug. 27, 1999

(51) Int. Cl.$^7$ .................... A61K 31/43; A61K 31/395
(52) U.S. Cl. ............................ 514/199; 514/210
(58) Field of Search ...................... 514/199, 210

(56) References Cited

U.S. PATENT DOCUMENTS

| | | |
|---|---|---|
| 4,309,438 | 1/1982 | Christensen et al. . |
| 4,479,947 | 10/1984 | Christensen et al. . |
| 4,539,208 | 9/1985 | Kahan et al. . |
| 5,494,666 | 2/1996 | Bohringer et al. . |
| 5,637,579 | 6/1997 | Hubschwerlen et al. . |
| 5,756,725 | 5/1998 | Wilkening et al. . |

FOREIGN PATENT DOCUMENTS

| | | |
|---|---|---|
| 0 007 614 | 2/1980 | (EP) . |
| 0 072 014 | 2/1983 | (EP) . |

OTHER PUBLICATIONS

Remington: the Science and Practice of Pharmacy, 19th Edition Mack Publishing Co., chapter 76, pp. 1298–1299, 1995.*

\* cited by examiner

Primary Examiner—Frederick Krass
Assistant Examiner—Donna Jagoe
(74) Attorney, Agent, or Firm—Sylvia A. Ayler; Mark R. Daniel

(57) ABSTRACT

The present invention relates to novel 2-(naphthosultamyl) methyl-carbapenem antibacterial agents or pharmaceutically acceptable salts thereof in combination with other β-lactams, which are useful in treating and preventing enterococcal infections. The combinations have anti-PBP5 activity as well as activity against the critical PBPs of sensitive isolates. The antibacterial compositions of the present invention thus comprise an important contribution to therapy for treating infections caused by these difficult to control pathogens.

This combination is also useful against gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS).

15 Claims, 4 Drawing Sheets

CARBAPENEM ANTIBACTERIAL COMPOSITIONS AND METHODS OF THE TREATMENT

BACKGROUND OF THE INVENTION

Within the last decade, enterococcus has become the second most common pathogen isolated in nosocomial infections. The ability of recent enterococcal isolates (i.e., *Enterococcus* (*E.*) *faecium, Enterococcus* (*E.*) *faecalis*) to rapidly acquire multidrug resistance to all available antimicrobials and to disseminate resistance determinants through the exchange of genetic elements has resulted in a serious therapeutic dilemma. Antibiotic resistance of enterococcus is characterized according to its susceptibility to two glycopeptides—vancomycin (VANCO) and teicoplanin (TEICO) and is accordingly divided into three major classes of VANCO resistant enterococci (VRE) (phenotypes VanA, VanB, VanC and perhaps even a new class). Enterococcal VanA isolates (*E. faecium* and *E. faecalis*) are resistant to high levels of VANCO (MIC≧64 µg/mL) and to TEICO (MIC≧16 µg/mL) and its plasmid transferable resistance is inducible by VANCO or TEICO, while class VanB isolates demonstrate moderate levels of resistance to VANCO (≈8–64 µg/mL and retain susceptibility to TEICO (MIC<2 µg/mL). Resistance to VanB isolates is induced by VANCO but is not thought to be transferable. Phenotypic class VanC VANCO resistance is found in *Enterococcus* (*E.*) *gallinarum* and *Enterococcus* (*E.*) *casseliflavus,* which possess low-level resistance to VANCO (MIC≧4 and ≦32 µg/mL) but retain susceptibility to TEICO (MIC≦1 µg/mL).

VanA resistant *E. faecium* (VREF) is intrinsically resistant to most β-lactam (cell-wall active) antibiotics by virtue of the relatively low affinity of their penicillin-binding proteins (PBPs), which are important enzymes in cell wall biosynthesis. β-lactam antibiotics inhibit bacterial growth through their binding of PBPs. Enterococci contain a normally low affinity PBP (PBP5) which in some recent isolates appears to be over produced and, in some cases, genetically modified.

Emergence of strains with resistance to most β-lactam, aminoglycoside and quinolone antibiotics when used as monotherapy have left only glycopeptides alone and in combination with aminoglycosides as the first line of defense against isolates resistant to β-lactam agents. For example, treatment of serious enterococcal infections usually includes combinations of VANCO with a number of moderately active β-lactams or aminoglycosides. However, this final therapeutic option is waning to the more recent isolation of enterococcal strains with high-level resistance to glycopeptides. Due to the isolation of enterococccal organisms that produce β-lactamases in addition to the discovery of VRE isolates with high resistance to nearly all β-lactam antibiotics, etc. (which usually occurs following monotherapy) an increased intensity in the search to discover new and innovative anti-enterococcal drugs is ever pressing.

SUMMARY OF THE INVENTION

The present invention relates to novel 2-(naphthosultamyl)methyl-carbapenem antibacterial agents or pharmaceutically acceptable salts thereof in combination with other antibiotics such as β-lactams, aminoglycosides, fluoroquinolones, related quinolones and naphthyridines, chloramphenicol, macrolides, ketolides, azalides, Synercid®, tetracyclines, glycopeptides, novobiocin, oxazolidinones and the like or a combination thereof. The combination is useful against gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS).

The present invention also relates to novel 2-(naphthosultamyl)methyl-carbapenem antibacterial agents or pharmaceutically acceptable salts thereof in combination with other β-lactams, which are useful in treating and preventing enterococcal infections. The combinations have anti-PBP5 activity as well as activity against the critical PBPs of sensitive isolates. The antibacterial compositions of the present invention thus comprise an important contribution to therapy for treating infections caused by these difficult to control pathogens.

Another aspect of the invention is concerned with the use of the novel antibiotic compositions in the treatment of bacterial infections.

DETAILED DESCRIPTION OF THE INVENTION

The present invention relates to novel 2-(naphthosultamy) methyl-carbapenem antibacterial agents (such as those disclosed in U.S. Pat. No. 5,756,725, herein incorporated by reference) in combination with other β-lactams, aminoglycosides, fluoroquinolones and the like. It is known that the response to a given combination may be strain specific and is not solely related to the level of sensitivity/resistance to the specific members of the combination. Thus, the combinations of the present invention are intended to be useful on all bacterial strains including those not mentioned herein.

One embodiment of the invention relates to compositions comprising a pharmaceutically acceptable carrier, a 2-(naphthosultamyl)methyl-carbapenem of structural formula I:

I or a pharmaceutically acceptable salt thereof, wherein:

$R^1$ represents H or methyl;

$CO_2M$ represents a carboxylic acid, a carboxylate anion, a pharmaceutically acceptable ester group or a carboxylic acid protected by a protecting group;

P represents hydrogen, hydroxyl, F or hydroxyl protected by a hydroxyl-protecting group;

each R is independently selected from: —R*; —Q; hydrogen; halo; —CN; —$NO_2$; —$NR^aR^b$; —$OR^c$; —$SR^c$; —$C(O)NR^aR^b$; —$C(O)OR^h$; —$S(O)R^c$; —$SO_2R^c$; —$SO_2NR^aR^b$; —$NR^aSO_2R^b$; —$C(O)R^a$; —$OC(O)R^a$; —$OC(O)NR^aR^b$; —$NR^aC(O)NR^bR^c$; —$NR^aCO_2R^h$; —$OCO_2R^h$; —$NR^aC(O)R^b$; —$C_{1-6}$ straight- or branched-chain alkyl, unsubstituted or substituted with one to four $R^d$ groups; and —$C_{3-7}$ cycloalkyl, unsubstituted or substituted with one to four $R^d$ groups;

each $R^a$, $R^b$ and $R^c$ independently represents hydrogen, —R*, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups;

or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups;

or $R^b$ and $R^c$ taken together with any intervening atoms represent a 4–6 membered saturated ring optionally interrupted by one to three of O, S, $NR^a$, with $R^a$ as defined above, or —C(O)—, said ring being unsubstituted or substituted with one to four $R^i$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —$C(NR^e)NR^fR^g$; —$NR^eC(NH)NR^fR^g$; —$NR^eC(NR^f)R^g$; —R* or —Q;

$R^e$, $R^f$ and $R^g$ represent hydrogen; —R*; —$C_{1-6}$ straight- or branched-chain alkyl unsubstituted or substituted with one to four $R^i$ groups;

or $R^e$ and $R^f$ taken together with any intervening atoms represent a 4–6 membered saturated ring optionally interrupted by one to three of O, S, —C(O)— or $NR^g$ with $R^g$ as defined above, said ring being unsubstituted or substituted with one to four $R^i$ groups;

each $R^i$ independently represents halo; —CN; —$NO_2$; phenyl; —$NHSO_2R^h$; —$OR^h$, —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents hydrogen, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

Q is selected from the group consisting of:

wherein:

a and b are 1, 2 or 3;

$L^-$ is a pharmaceutically acceptable counterion;

α represents O, S or $NR^s$;

β, δ, λ, μ and σ represent $CR^t$, N or $N^+R^s$, provided that no more than one of β, δ, λ, μ and σ is $N^+R^s$;

R* is selected from the group consisting of:

$$\begin{array}{ccc} \underset{d=y}{\overset{e}{\underset{}{\bigcirc}}}{-x}, & \underset{e-g}{\overset{x}{\underset{}{\bigcirc}}}{-d}\text{ and } & \underset{e-g}{\overset{x=y}{\underset{}{\bigcirc}}}{-z} \end{array}$$

wherein:

d represents O, S or $NR^k$;

e, g, x, y and z represent $CR^m$, N or $N^+R^k$, provided that no more than one of e, g, x, y and z in any given structure represents $N^+R^k$;

$R^k$ represents hydrogen; —$C_{1-6}$ straight- or branched-chain alkyl, unsubstituted or substituted with one to four $R^i$ groups; or —$(CH_2)_nQ$ where n=1, 2 or 3 and Q is as previously defined;

each $R^m$ independently represents a member selected from the group consisting of: hydrogen; halo; —CN; —$NO_2$; —$NR^nR^o$; —$OR^n$; —$SR^n$; —$CONR^nR^o$; —$COOR^h$; —$SOR^n$; —$SO_2R^n$; —$SO_2NR^nR^o$; —$NR^nSO_2R^o$; —$COR^n$; —$NR^nCOR^o$; —$OCOR^n$; —$OCONR^nR^o$; —$NR^nCO_2R^h$; —$NR^nCONR^oR^h$; —$OCO_2R^h$; —$CNR^nNR^oR^h$; —$NR^nCNHNR^oR^h$; —$NR^nC(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)_nQ$ where n and Q are as defined above;

$R^n$ and $R^o$ represent hydrogen, phenyl; —$C_{1-6}$ straight- or branched-chain alkyl unsubstituted or substituted with one to four $R^i$ groups;

each $R^s$ independently represents hydrogen; phenyl or —$C_{1-6}$ straight- or branched-chain alkyl, unsubstituted or substituted with one to four $R^i$ groups;

each $R^t$ independently represents hydrogen; halo; phenyl; —CN; —$NO_2$; —$NR''R^v$; —$OR''$; —$SR''$; —$CONR''R^v$; —$COOR^h$; —$SOR''$; —$SO_2R''$; —$SO_2NR''R^v$; —$NR''SO_2R^v$; —$COR''$; —$NR''COR^v$; —$OCOR''$; —$OCONR''R^v$; —$NR''CO_2R^v$; —$NR''CONR^vR^w$; —$OCO_2R^v$; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

or $R^u$ and $R^v$ together with any intervening atoms represent a 4–6 membered saturated ring optionally interrupted by one or more of O, S, $NR^w$ or —C(O)—, said ring being unsubstituted or substituted with one to four $R^i$ groups;

each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

or $R^h$ and $R^w$ taken together with any intervening atoms represent a 5–6 membered saturated ring, optionally interrupted by one or two of O, S, $SO_2$, NH or $NCH_3$;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—;

or $R^x$ and $R^y$ together with any intervening atoms represent a 4–6 membered saturated ring optionally interrupted by O, S, $SO_2$, $NR^w$, $N^+R^hR^w$ or —C(O)—, unsubstituted or substituted with 1–4 $R^i$ groups, and when $R^x$ and $R^y$ together represent a 4–6 membered ring as defined above, $R^z$ is as defined above or $R^z$ represents an additional saturated 4–6 membered ring fused to the ring represented by $R^x$ and $R^y$ taken together, optionally interrupted by O, S, $NR^w$ or —C(O)—, said rings being unsubstituted or substituted with one to four $R^i$ groups;

and another antibiotic including β-lactams such as carbapenems, cephalosporins (ceftriaxone), penicillins; aminoglycosides (as exemplified by gentamicin and including but not limited to amikacin, dibekacin, streptomycin, neomycin, kanamycin, spectinomycin, kasugamycin); fluoroquinolones (as exemplified by ciprofloxacin and including but not limited to trovafloxacin, sparfloxacin, gatifloxacin, grepafloxacin, ofloxacin, norfloxacin, floxin, levofloxacin) and related quinolones and naphthyridines with activity against topoisomerases; chloramphenicol; as well as macrolides, ketolides, azalides (and other related polyketides), Synercid®, tetracyclines (including glycylcyclines), glycopeptides (including, but not limited to, vancomycin, teicoplainin, LY-333328), novobiocin (and coumermycin) and oxazolidinones or a combination thereof.

The invention is described herein in detail using the terms defined below unless otherwise specified.

Carboxylate anion refers to a negatively charged group —COO—.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, selected from $R^d$ and $R^i$, as defined, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a hydrocarbon radical straight or branched, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole. Examples include the following:

pyrrole (pyrrolyl)

imidazole (imidazolyl)

thiazole (thiazolyl)

oxazole (oxazolyl)

furan (furyl)

thiophene (thienyl)

triazole (triazolyl)

pyrazole (pyrazolyl)

isoxazole (isoxazolyl)

-continued isothiazole (isothiazolyl)    pyridine (pyridinyl)    pyrazine (pyrazinyl)

pyridazine (pyridazinyl)    pyrimidine (pyrimidinyl)    triazine (triazinyl)

Heteroarylium refers to heteroaryl groups bearing a quaternary nitrogen atom and thus a positive charge. Examples include the following:

When a charge is shown on a particular nitrogen atom in a ring which contains one or more additional nitrogen atoms, it is understood that the charge may reside on a different nitrogen atom in the ring by virtue of charge resonance that occurs.

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The terms "quaternary nitrogen" and "positive charge" refer to tetravalent, positively charged nitrogen atoms including, e.g., the positively charged nitrogen in a tetraalkylammonium group (e.g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

Halogen and "halo" refer to bromine, chlorine, fluorine and iodine.

Alkoxy refers to $C_1$–$C_4$ alkyl—O—, with the alkyl group optionally substituted as described herein.

When a group is termed "substituted", unless otherwise indicated, this means that the group contains from 1 to 4 substituents thereon. With respect to R, $R^a$, $R^b$ and $R^c$, the substituents available on alkyl groups are selected from the values of $R^d$. Many of the variable groups are optionally substituted with up to four $R^i$ groups. With respect to $R^e$, $R^f$ and $R^g$, when these variables represent substituted alkyl, the substituents available thereon are selected from the values of $R^i$.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, N.Y. (1991). Examples of suitable protecting groups are contained throughout the specification.

In some of the carbapenem compounds of the present invention, M is a readily removable carboxyl protecting group, and/or P represents a hydroxyl which is protected by a hydroxyl-protecting group. Such conventional protecting groups consist of known groups which are used to protectively block the hydroxyl or carboxyl group during the synthesis procedures described herein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups include allyl, benzhydryl, 2-naphthylmethyl, benzyl, silyl such as t-butyldimethylsilyl (TBDMS), phenacyl, p-methoxybenzyl, o-nitrobenzyl, p-methoxyphenyl, p-nitrobenzyl, 4-pyridylmethyl and t-butyl.

Examples of suitable C-6 hydroxyethyl protecting groups include triethylsilyl, t-butyldimethylsilyl, o-nitrobenzyloxycarbonyl, p-nitrobenzyloxycarbonyl, benzyloxycarbonyl, allyloxycarbonyl, t-butyloxycarbonyl, 2,2,2-trichloroethyloxycarbonyl and the like.

The carbapenems of this invention, other than the novel 2-(naphthosultamyl)methyl-carbapenem described above, includes imipenem (plus or minus cilastatin), meropenem, biapenem, panipenem, (4R,5S,6S)-3-[3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid, an enantiomer, diastereomer or pharmaceutically acceptable salt thereof.

The β-lactams included in this invention include carbapenems such as imipenem (plus or minus cilastatin; with cilastatin=Primaxin®), meropenem, biapenem, panipenem, (4R,5S,6S)-3-[3S,5S)-5-(3-carboxyphenylcarbamoyl) pyrrolidin-3-ylthio]-6-(1R)-1-hydroxyethyl]-4-methyl-7- oxo-1-azabicyclo[3.2.0]hept-2-ene-2-carboxylic acid, an enantiomer, diastereomer or pharmaceutically acceptable salt thereof and the like, cephalosporins and cephamycins such as cefoperazone, cefotiam, cefpirome, cefmetazole, cafazolin, cephalexin, cefuroxime, cefaclor, cefotaxime, ceftriaxone, moxalactam, cefixime and the like and penicillins such as ampicillin, amoxicillin, piperacillin, nafcillin, oxacillin, cloxacillin and combinations of penicillins with a beta-lactamase inhibitor such as sulbactam, clavulanic acid, tazobactam, and the like.

The carbapenem compositions of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds.

With respect to —$CO_2M$, which is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a protecting group (M represents a carboxyl protecting group). The pharmaceutically acceptable salts referred to above may take the form —COOM, where M is a negative charge, which is balanced by a counterion, e.g., an alkali metal cation such as sodium or potassium. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

The pharmaceutically acceptable esters are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. These are also referred to as "biolabile esters".

Biolabile esters are biologically hydrolizable, and may be suitable for oral administration, due to good absorption through the stomach or intestinal mucosa, resistance to gastric acid degradation and other factors. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties.: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

$L^-$ can be present or absent as necessary to maintain the appropriate charge balance. When present, $L^-$ represents a pharmaceutically acceptable counterion. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate and tosylate. Other suitable anionic species will be apparent to the ordinarily skilled chemist.

Likewise, when L– represents a species with more than one negative charge, such as malonate, tartrate or ethylenediamine-tetraacetate (EDTA), an appropriate number of carbapenem molecules can be found in association therewith to maintain the overall charge balance and neutrality.

It is preferred that least one of the R groups attached to the naphtho-sultam platform contains a positively charged moiety. Thus, it can include —R* or Q, or a moiety which in turn contains a positively charged group.

Yet another embodiment of this invention is realized when the compounds of structural formula I are represented by formula Ie:

Ie or a pharmaceutically acceptable salt thereof, wherein:

R contains a positively charged moiety selected from the group consisting of: —R*, Q, and a $C_{1-6}$ straight or branched alkyl chain substituted with one $R^d$ group;

$R^d$ is independently selected —R* or Q;

Q is selected from the group consisting of:

wherein L⁻, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Still another embodiment of the invention is realized when the compounds of formula I are:
(1S,5R,6S)-2-(5-(((carbamoylmethyl)-1,4-diazoniabicyclo[2.2.2]oct-1-yl)methyl)(1,8-naphthosultam)methyl)-6-[1(R)-hydroxyethyl]-1-methylcarbapen-2-em-3-carboxylate chloride;
(1S,5R,6S)-2-(5-(((3-hydroxyprop-1-yl)-1,4-diazoniabicyclo[2.2.2]oct-1-yl)methyl)(1,8-naphthosultam)methyl)-6-[1(R)-hydroxyethyl]-1-methylcarbapen-2-em-3-carboxylate chloride;
(1S,5R,6S)-2-(5-((1-methylimidazol-3-ium)methyl)(1,8-naphthosultam)methyl)-6-[1(R)-hydroxyethyl]-1-methylcarbapen-2-em-3-carboxylate;
(1S,5R,6S)-2-(5-(((2-(1-methylimidazol-3-ium)-ethyl)(1,8-naphthosultam)methyl)-6-[1(R)-hydroxyethyl]-1-methylcarbapen-2-em-3-carboxylate;
(1S,5R,6S)-2-(4-(((carbamoylmethyl)-1,4-diazoniabicyclo[2.2.2]oct-1-yl)methyl)(1,8-naphthosultam)methyl)-6-[1(R)-hydroxyethyl]-1-methylcarbapen-2-em-3-carboxylate chloride;
(1S,5R,6S)-2-(4-(2-(((carbamoylmethyl)-1,4-diazoniabicyclo[2.2.2]oct-1-yl))-ethyl)(1,8-naphthosultam)methyl)-6-[1(R)-hydroxyethyl]-1-methylcarbapen-2-em-3-carboxylate chloride;
(1S,5R,6S)-2-(4-(2-(((3-hydroxyprop-1-yl)-1,4-diazoniabicyclo[2.2.2]oct-1-yl))-ethyl)(1,8-naphthosultam)methyl)-6-[1(R)-hydroxyethyl]-1-methylcarbapen-2-em-3-carboxylate chloride; or
(1S,5R,6S)-2-(4-(2-((1-methylimidazol-3-ium))-ethyl)(1,8-naphthosultam)methyl)-6-[1(R)-hydroxyethyl]-1-methylcarbapen-2-em-3-carboxylate.

A preferred embodiment of the invention is realized when the compounds of formula I are:
(1S,5R,6S)-2-(5-(((carbamoylmethyl)-1,4-diazoniabicyclo[2.2.2]oct-1-yl)methyl)(1,8-naphthosultam)methyl)-6-[1(R)-hydroxyethyl]-1-methylcarbapen-2-em-3-carboxylate chloride;
(1S,5R,6S)-2-(4-(((carbamoylmethyl)-1,4-diazoniabicyclo[2.2.2]oct-1-yl)methyl)(1,8-naphthosultam)methyl)-6-[1(R)-hydroxyethyl]-1-methylcarbapen-2-em-3-carboxylate chloride; or
(1S,5R,6S)-2-(4-(2-(((carbamoylmethyl)-1,4-diazoniabicyclo[2.2.2]oct-1-yl))ethyl)(1,8-naphthosultam)methyl)-6-[1(R)-hydroxyethyl]-1-methylcarbapen-2-em-3-carboxylate chloride.

Another preferred embodiment of the invention is realized when the other antibiotic employed is selected from the group consisting of cephalosporins, penicillins, gentamicin, ciprofloxacin, imipenem, meropenem, chloramphenicol, vancomycin, or teicoplainin.

In yet another aspect of this invention, the novel antibacterial compositions of this invention comprise a pharmaceutically acceptable carrier, a therapeutically effective amount of a 2-(naphthosultamyl)methyl-carbapenem selected from
(1S,5R,6S)-2-(5-(((carbamoylmethyl)-1,4-diazoniabicyclo[2.2.2]oct-1-yl)methyl)(1,8-naphthosultam)methyl)-6-[1(R)-hydroxyethyl]-1-methylcarbapen-2-em-3-carboxylate chloride;
(1S,5R,6S)-2-(4-(((carbamoylmethyl)-1,4-diazoniabicyclo[2.2.2]oct-1-yl)methyl)(1,8-naphthosultam)methyl)-6-[1(R)-hydroxyethyl]-1-methylcarbapen-2-em-3-carboxylate chloride; and
(1S,5R,6S)-2-(4-(2-(((carbamoylmethyl)-1,4-diazoniabicyclo[2.2.2]oct-1-yl))-ethyl)(1,8-naphthosultam)methyl)-6-[1(R)-hydroxyethyl]-1-methylcarbapen-2-em-3-carboxylate chloride; and a therapeutically effective amount of another antibiotic selected from carbapenems, cephalosporins (ceftriaxone), penicillins; aminoglycosides (as exemplified by gentamicin and including but not limited to amikacin, dibekacin, streptomycin, neomycin, kanamycin, spectinomycin, kasugamycin); fluoroquinolones (as exemplified by ciprofloxacin and including but not limited to trovafloxacin, sparfloxacin, gatifloxacin, grepafloxacin, ofloxacin, norfloxacin, floxin, levofloxacin) and related quinolones and naphthyridines with activity against topoisomerases; chloramphenicol; as well as macrolides, ketolides, azalides (and other related polyketides), Synercid®, tetracyclines (including glycylcyclines), glycopeptides (including, but not limited to, vancomycin, teicoplainin, LY-333328), novobiocin (and coumermycin) and oxazolidinones or a combination thereof.

An aspect of this invention is realized when the 2-(naphthosultamyl)methyl-carbapenem is (1S,5R,6S)-2-(4-(2-(((carbamoylmethyl)-1,4-diazoniabicyclo[2.2.2]oct-1-yl))-ethyl)(1,8-naphthosultam)methyl)-6-[1(R)-hydroxyethyl]-1-methylcarbapen-2-em-3-carboxylate chloride; and the other antibiotic selected is from cephalosporins, penicillins, gentamicin, ciprofloxacin, imipenem, meropenem, (4R,5S,6S)-3-[(3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid, chloramphenicol, vancomycin, and teicoplainin.

Another embodiment of this invention relates to 2-(naphthosultamyl)methyl-carbapenem antibacterial agents or ophthamologically acceptable salts thereof, described above, in combination with other carbapenems.

An aspect of this invention is realized when the other carbapenem is (4R,5S,6S)-3-[(3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid, imipenem, or meropenem from about 1 to about 100 mg/kg, preferably about 2 to about 50 mg/kg and the 2-(naphthosultamyl)methyl-carbapenem is (1S,5R, 6S)-2-(4-(2-(((carbamoylmethyl)-1,4-diazoniabicyclo [2.2.2]oct-1-yl))-ethyl)(1,8-naphthosultam)methyl)-6-[1 (R)-hydroxyethyl]-1-methylcarbapen-2-em-3-carboxylate chloride, from about 0.1 to about 50 mg/kg, preferably about 0.5 to about 20 mg/kg.

Another embodiment of this invention relates to from about novel 2-(naphthosultamyl)methyl-carbapenem antibacterial agents or ophthamologically acceptable salts thereof, described above, in combination with fluoroquinolones, aminoglycosides, or chloramphenicol or a combination thereof.

An aspect of this invention is realized when the fluoroquinolone is ciprofloxacin, from about 0.1 to about 40 mg/kg, preferably about 0.5 to about 20 mg/kg of the aminoglycoside is gentamicin from about 0.5 to about 12 mg/kg, and the 2-(naphthosultamyl)methyl-carbapenem is (1S,5R,6S)-2-(4-(2-(((carbamoylmethyl)-1,4-diazoniabicyclo[2.2.2]oct-1-yl))-ethyl)(1,8 -naphthosultam)methyl)-6-[1(R)-hydroxyethyl]-1-methylcarbapen-2-em-3-carboxylate chloride, from about 0.1 to about 50 mg/kg, preferably about 0.5 to about 20 mg/kg.

Still another embodiment of this invention relates to novel 2-(naphthosultamyl)methyl-carbapenem antibacterial agents or ophthamologically acceptable salts thereof, described above, in combination with a imipenem or meropenem and another antibiotic selected from cephalosporins, penicillins, gentamicin, ciprofloxacin, chloramphenicol, vancomycin, or teicoplainin.

The compositions of the present invention are valuable as antibacterial agents active against enterococcal infections, particularly against clinical isolates of multiply resistant *E. faecium*. The compositions of the present invention are also valuable as antibacterial agents active against various gram positive and gram negative bacteria. Many of compositions of the present invention are also biologically active against MRSA/MRCNS.

Suitable subjects for the administration of the formulation of the present invention include mammals, primates, man, and other animals. In vitro antibacterial activity is predictive of in vivo activity when the compositions are administered to a mammal infected with a susceptible bacterial organism.

Using standard susceptibility tests, the compositions of the invention are determined to be active against MRSA and enterococcal infections.

The compounds of the invention are formulated in pharmaceutical compositions by combining the compounds with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophilized or non-lyophilized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The novel antibiotic compositions of this invention for human delivery per unit dosage, whether liquid or solid, comprise from about 0.01% to as high as about 99% of the 2-(naphthosultamyl)methyl-carbapenem discussed herein, the preferred range being from about 10–60% and from about 1% to about 99.99% of one or more of other antibiotics such as those discussed herein, preferably from about 40% to about 90%. The composition will generally contain from about 125 mg to about 3.0 g of the 2-(naphthosultamyl)methyl-carbapenem discussed herein; however, in general, it is preferable to employ dosage amounts in the range of from about 250 mg to 1000 mg and from about 200 mg to about 5 g of the other antibiotics discussed herein; preferably from about 250 mg to about 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal the claimed composition in an amount effective to treat said infection.

The preferred methods of administration of the claimed compositions include oral and parenteral, e.g., i.v. infusion, i.v. bolus and i.m. injection formulated so that a unit dosage comprises a therapeutically effective amount of each active component or some submultiple thereof.

For adults, about 5–50 mg/kg of body weight, preferably about 250 mg to about 1000 mg per person of the 2-(naphthosultamyl)methyl-carbapenem antibacterial compound and about 250 mg, to about 1000 mg per person of the other antibiotic(s) given one to four times daily is preferred. More specifically, for mild infections a dose of about 250 mg two or three times daily of the 2-(naphthosultamyl)methyl-carbapenem antibacterial compound and about 250 mg two or three times daily of the other antibiotic is recommended. For moderate infections against highly susceptible gram positive organisms a dose of about 500 mg each of the 2-(naphthosultamyl)methyl-carbapenem and the other antibiotics, three or four times daily is recommended. For severe, life-threatening infections against organisms at the upper limits of sensitivity to the antibiotic, a dose of about 500–2000 mg each of the 2-(naphthosultamyl)methyl-carbapenem and the other antibiotics, three to four times daily may be recommended.

For children, a dose of about 5–25 mg/kg of body weight given 2, 3, or 4 times per day is preferred; a dose of 10 mg/kg is typically recommended.

The claimed compositions contain antibiotic agents which are of the broad class known as carbapenems. Many carbapenems are susceptible to attack by a renal enzyme known as dehydropeptidase (DHP). This attack or degradation may reduce the efficacy of the carbapenem antibacterial agent. Many of the compounds of the present invention, on the other hand, are less subject to such attack, and therefore may not require the use of a DHP inhibitor. However, such use is optional and contemplated to be part of the present invention. Inhibitors of DHP and their use with carbapenems are disclosed in, e.g.,[European Patent Application Nos. 79102616.4, filed Jul. 24, 1979 (Patent No. 0 007 614); and 82107174.3, filed Aug. 9, 1982 (Publication No. 0 072 014)].

The compositions of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. It is preferred that a pharmaceutically acceptable amount of cilastatin is administered with the carbapenems. A preferred weight ratio of DHP to carbapenem: DHP inhibitor in the combination compositions is about 1:1. The amount of DHP to employed generally can be determined by the skilled artisan. U.S. Pat. No. 4,539,208, herein incorporated by reference illustrates the amount of DHP that can be used with a carbapenem.

A preferred DHP inhibitor is 7-(L-2-amino-2-carboxyethylthio)-2-(2,2-dimethylcyclopropanecarboxamide)-2-heptenoic acid or a useful salt thereof. Thus, another aspect of this invention is realized when the 2-(naphthosultamyl)methyl-carbapenem antibacterial agents or ophthamologically acceptable salts thereof, described above, are in combination with imipenem or meropenem containing 7-(L-2-amino-2-carboxy-ethylthio)-2-(2,2-dimethylcyclopropanecarboxamide)-2-heptenoic acid or a useful salt thereof. When imipenem contains cilastatin it is preferred that composition is Primaxin®.

The invention is further described in connection with the following non-limiting examples.

EXAMPLE 1

The relative in-vivo protective abilities of (1S,5R,6S)-2-(4-(2-(((carbamoylmethyl)-1,4-diazoniabicyclo[2.2.2]oct-1-yl))-ethyl)(1,8-naphthosultam)methyl)-6-[1(R)-hydroxyethyl]-1-methylcarbapen-2-em-3-carboxylate chloride (Compound A) in combination with imipenem (IPM) to influence clearance of CL5053 from local soft tissue (thigh) was measured in a cyclophosphamide-treated mouse model. Multple antibiotic treatments were administered (s.c.) over a 5 day period. Tissues were aseptically removed on day +7 and processed.

Materials and Methods
Localized Tissue Infection Model
Bacterial Culture Preparation Stock cultures of *E. faecium* CL5053 (obtained from Bellevue Hospital in NYC) were prepared from slants or L-tubes. A shake flask containing ~75 mL of trypticase soy broth (TSB) was inoculated with ~1 mL of seed culture followed by shaking at 250 rpm for 10–12 hours at 35° C. The culture was then washed (i.e., centrifuged in a Sorvall RC-5B at 5000 rpm ~15 min and bacterial cells concentrated twofold [to ~$10^9$ to $10^{10}$ colony forming units (CFU/mL)] in fresh TSB containing 10% glycerol (or in PBS-10% glycerol) by reconstituting the pellet in ~half the original volume. Finally, ~1 mL aliquots of the washed stock culture was stored in −70° C. for later use to initiate cultures for animal infections.

Prior to infection, 1 mL of the above frozen culture was thawed in cold $H_2O$, warmed to 35° C. and added to ~75 mL fresh TSB before incubating at 35° C. for ~10 hours as described above. The 10 hour culture was then washed as above to remove media containing toxins, etc. released during cell growth and bacterial death. The cell pellet was then reconstituted with fresh TSB in half the original volume. 0.2 mL of the washed, concentrated culture (challenge inoculum) was injected intramuscularly (i.m.) into the right thighs of mice. Infected mice were further divided into appropriate groups of 5 or 10 animals each for antibiotic treatments.

Antibiotic Preparations

The antibiotics of this invention were prepared in 10 mM 3-[-Morpholinolpropanesulfonic acid (MOPS) buffer, pH 7.1. For all carbapenems, the above MOPS buffer also contains cilastatin, a renal dehydropeptidase-I (DHP-1) inhibitor, at a concentration which would yield a final dose of 40 mg/kg in a 0.5 mL inoculum/mouse regardless of antibiotic concentration. Antibiotic dosing (s.c. in 0.5 mL) was initiated one hour following bacterial challenge (+1 hour), followed by two treatments at four hour intervals (+5 and +9 hours). Over the next 5 days, further antibiotic treatments were administered once or twice daily (at ~10 to 12 and at ~24 hour intervals, respectively) starting at ~+20 hours and continuing for a total of either 8 or 13 treatments. Two days after the last antibiotic treatment (day +7), animals were sacrificed and thigh tissues were prepared for CFU determination.

Animals

Random outbred CD 1 mice (Charles River Labs) were immunocompromised by a single injection of cyclophosphamide (Cytoxan) prepared in PBS at a final concentration of 250 mg/kg/0.5 mL/mouse −4 days prior to i.m. bacterial challenge with *E. faecium* CL5053. Immediately before or after bacterial challenge, 0.5 mL of a 0.45 µm membrane filtered ferric iron ($Fe^{+3}$)/PBS solution was injected i.p. at 20 mg/kg. The source of $Fe^{+3}$ was obtained by appropriate PBS solubilization of ferric ammonium citrate (consisting of 18.5% $Fe^{+3}$ by weight) followed by filtering through a 0.45 µm membrane just prior to its i.p. administration at the time of bacterial challenge.

Preparation of Tissue for Detection of Colony Forming Units (CFU)

On day +7 mice were euthanized, the lower abdomen and thighs were flushed with 70% ethanol and the outer skin aseptically removed. Denuded thigh tissues were aseptically collected and placed in tubes containing 4 mL of sterile PBS/10% glycerol for temporary −70° C. storage or for same day processing. On the day of plating, frozen thighs were thawed in cold $H_2O$, ground with a Polytron homogenizer for 5–10 seconds each and placed on ice for further dilutions. Tenfold serial dilutions of each sample were made in tubes containing 0.9 mL of cold fresh TSB prior to plating 0.1 mL from selected dilution tubes onto Enterococcus-specific m-Enterococcus agar plates. Plates were incubated at 35° C. for 2 to 3 days and the number of CFU's remaining per thigh determined.

Results

Figure 1:
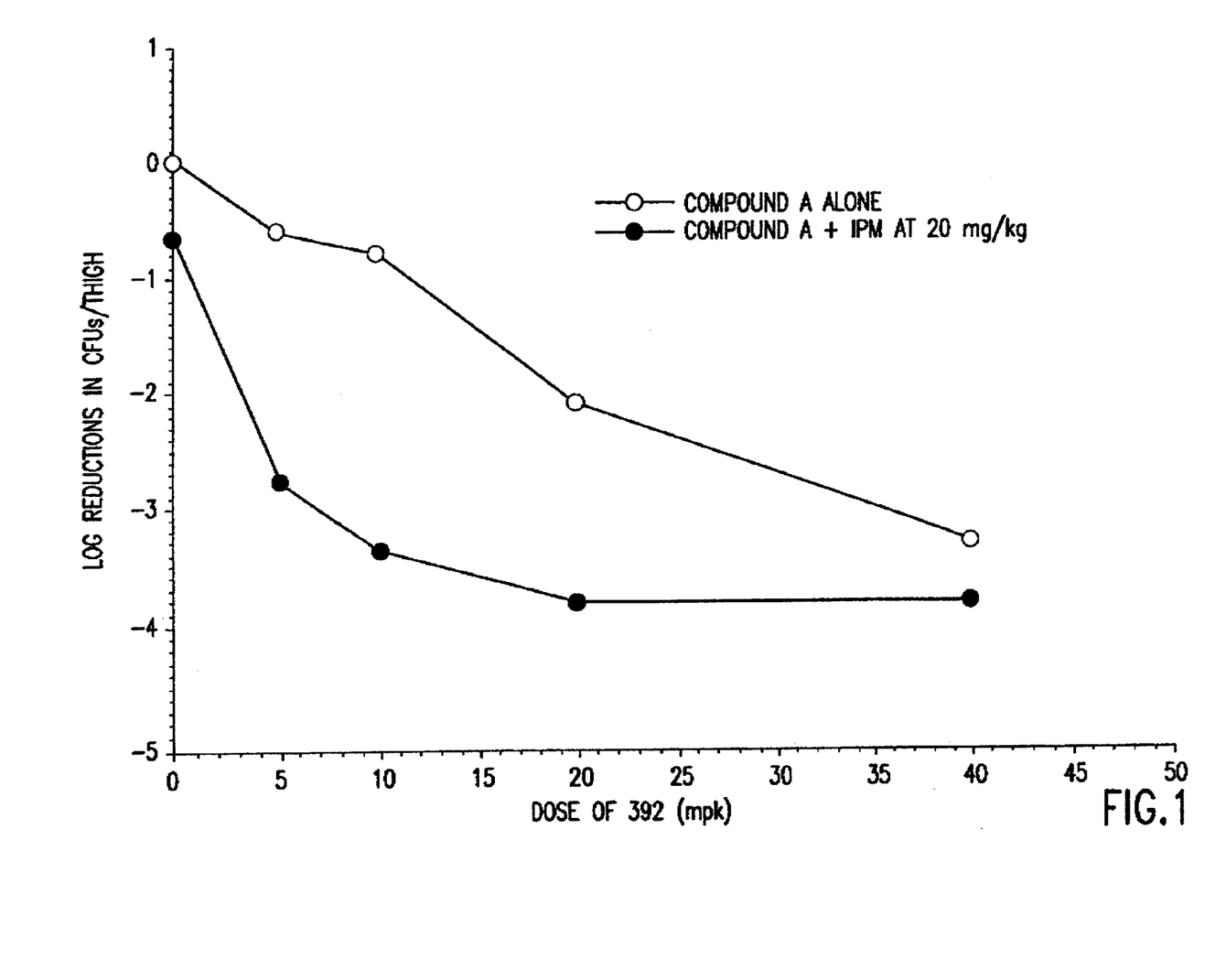
FIG. 1 shows the effect of Compound A (described below), at various concentrations, alone and in combination with imipenem (20 mg/kg) in treating VanA-resistant *E. faecium* CL5053 using the Mouse Thigh Model. Bacterial clearance is expressed in $\log_{10}$ reductions in CFUs.

FIG. 1 show that Compound A alone effectively protects mice (reducing 3.3, 2.08, ~0.8 and 0.6 logs of CFU, respectively with 40, 20, 10 and 5 mg/kg). However, combinations of Compound A with a fixed amount of IPM (20 mg/kg)

were significantly synergistic (e.g., 0.20 mg/kg of IPM increased the effective log clearance of 5 mg/kg of Compound A from 0.6 to 2.75 logs).

EXAMPLE 2

To evaluate the combination of Compound A with gentamicin to influence clearance of $Van^R Gent^S Amp^S$ (where R=resistant and S=sensitive) *E. faecalis* CL 5244 (obtained from Washington University School of Medicine, St. Louis, Mo.) partial checkerboard synergy studies were performed followed by time-kill studies.

To evaluate the combination of Compound A with ciprofloxacin to influence clearance of $Van^R Gent^S Amp^S$ (where R=resistant and S=sensitive) *E. faecalis* CL 4877 (obtained from University of Maryland Hospital, University of Maryland Medical System, 22 South Green St., Baltimore, Md. 21201) partial checkerboard synergy studies were also performed followed by time-kill studies.

Materials and Methods

Antibiotics

Compound A stock solution was prepared in 10 mM MOPs buffer, pH 7.0, and its concentration confirmed using a spectrophotometric assay. Gentamicin (Sigma Chemical Co.) stock solutions were prepared in 10 mM MOPs buffer, pH 7.0 on a weight per volume basis.

Bacterial Strains

*E. faecalis*, *E. faecium* and *E. gallinarum* strains were provided by the Merck Clinical Culture Collection.

Media

Organisms maintained on Brain Heart Infusion (BHI) (Difco) agar slants were grown overnight in BHI broth (Difco) prior to testing. The test medium used was BHI broth.

MIC Determinations

MICs were determined by broth microdilution. Serial twofold dilutions of each antibiotic were prepared in BHI broth and inoculated with ~$10^6$ CFU/mL. The MIC is defined as the lowest concentration of antibiotic that resulted in no visible growth after incubation at 35° C. for 22 hours.

Checkerboard and Time-Kill Synergy Studies

Serial twofold antibiotic dilutions were prepared in BHI broth and inoculated with ~$10^6$ CFU/mL. Follow-up time-kill studies were done in flasks. Compound A or Compound A in combination with gentamicin (at clinically relevant concentrations) were added to flasks containing BHI broth (50 mL/flask), inoculated with ~$10^6$ CFU/mL and incubated at 35° C. with shaking at 85 rpm. Viable counts were obtained at appropriate time intervals on BHI agar plates.

Results

Figure 2:
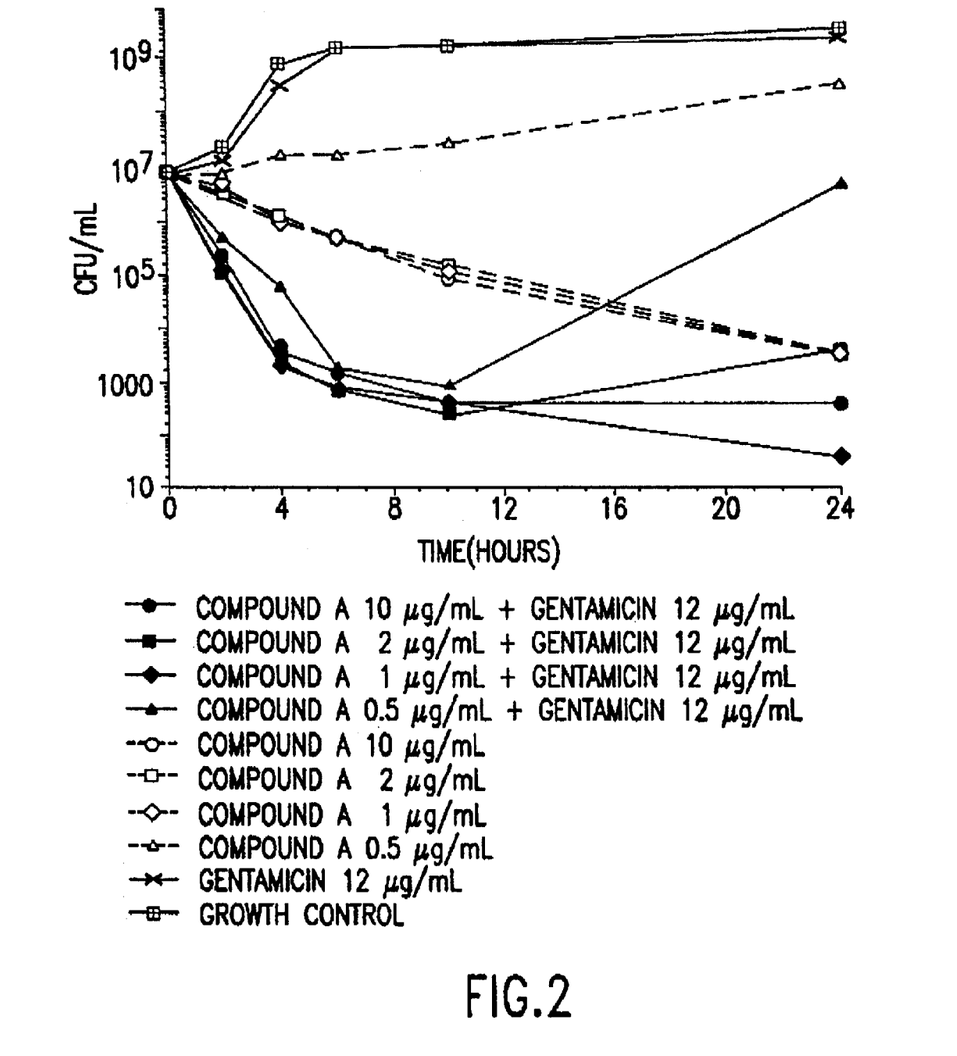
FIG. 2. shows the rate of kill of Van$^R$Gent$^S$Amp$^S$ *E. faecalis* CL5244 by Compound A (described below), at various concentrations, alone and in combination with 12 µg/mL of gentamicin.

FIG. 2 shows that Compound A alone is effective against $Van^R Gent^S Amp^S$ *E. faecalis* CL 5244. However, combinations of Compound A with a fixed amount of gentamicin were significantly synergistic.

Figure 3:
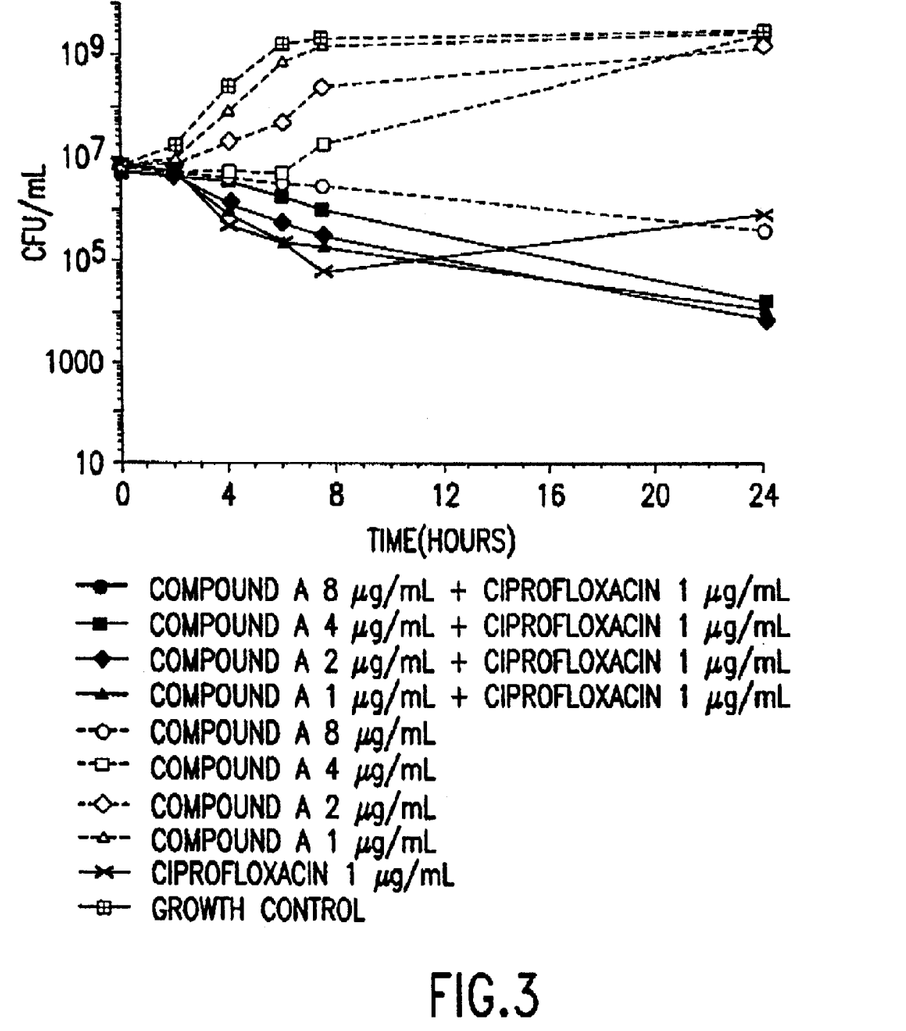
FIG. 3. shows the rate of kill of Van$^R$Gent$^S$Amp$^S$ *E. faecalis* CL4877 by Compound A (described below), at various concentrations, alone and in combination with 1.0 µg/mL of ciprofloxacin.
Figure 4:
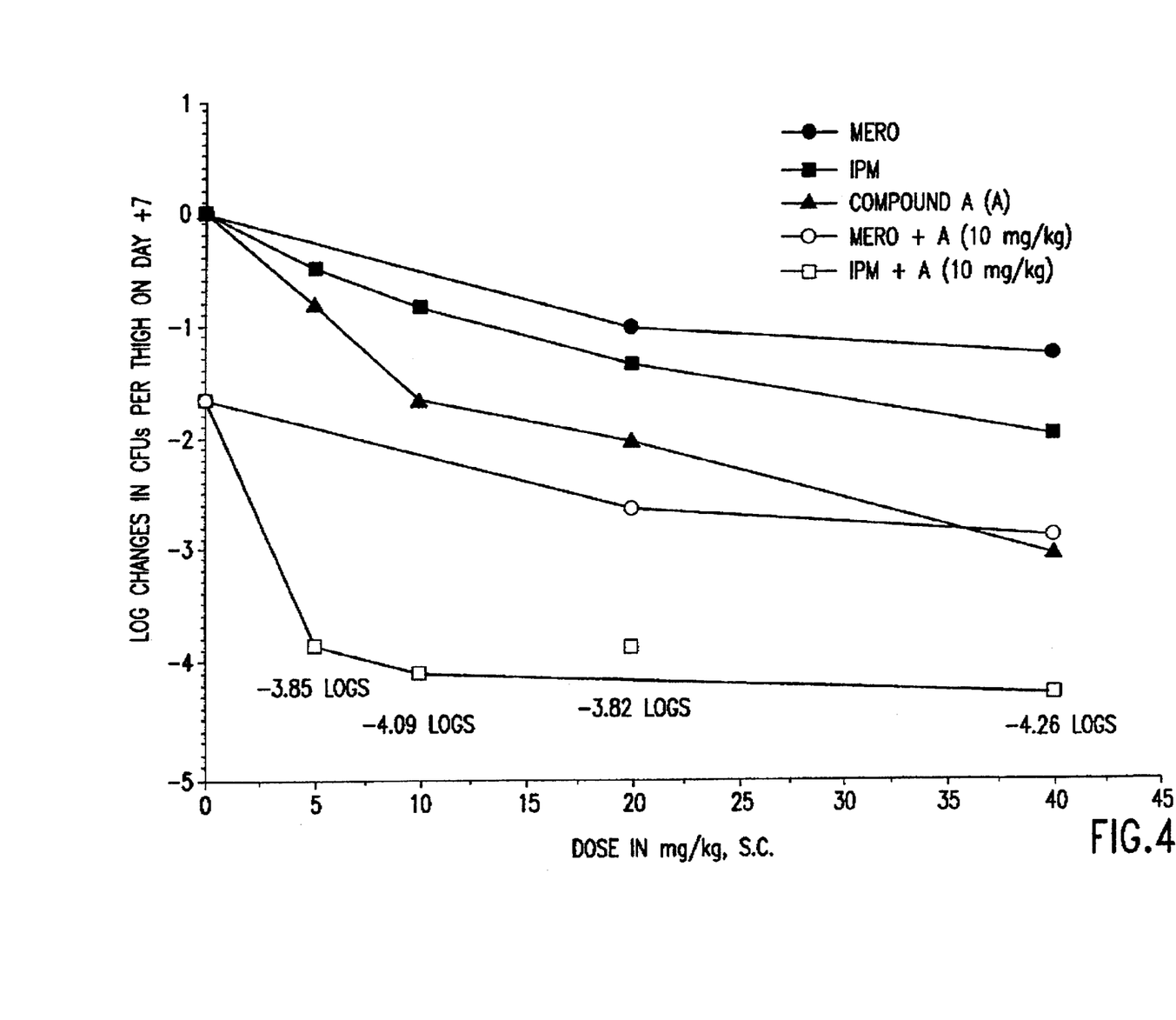
FIG. 4. shows the effect of Compound A (10 mg/kg) and varying amounts of imipenem and meropenem as well as Compound A (10 mg/kg) in combination with varying amounts of imipenem or meropenem in treating VanA-resistant *E. faecium* CL5053.

FIG. 3 shows that Compound A alone is effective against $Van^R Gent^S Amp^S$ *E. faecalis* CL 4877. However, combinations of Compound A with a fixed amount of ciprofloxacin were significantly effective.

What is claimed is:

1. An antibiotic composition comprising a pharmaceutically acceptable carrier, a 2-(naphthosultamyl)methyl-carbapenem of structural formula I:

or a pharmaceutically acceptable salt thereof, wherein:
$R^1$ represents H or methyl;
$CO_2M$ represents a carboxylic acid, a carboxylate anion, a pharmaceutically acceptable ester group or a carboxylic acid protected by a protecting group;
P represents hydrogen, hydroxyl, F or hydroxyl protected by a hydroxyl-protecting group;
each R is independently selected from: —$R^*$; —Q; hydrogen; halo; —CN; —$NO_2$; —$NR^a R^b$; —$OR^c$; —$SR^c$; —$C(O)NR^a R^b$; —$C(O)OR^h$; —$S(O)R^c$; —$SO_2 R^c$; —$SO_2 NR^a R^b$; —$NR^a SO_2 R^b$; —$C(O)R^a$; —$OC(O)R^a$; —$OC(O)NR^a R^b$; —$NR^a C(O)NR^b R^c$; —$NR^a CO_2 R^h$; —$OCO_2 R^h$; —$NR^a C(O)R^b$; —$C_{1-6}$ straight- or branched-chain alkyl, unsubstituted or substituted with one to four $R^d$ groups; and —$C_{3-7}$ cycloalkyl, unsubstituted or substituted with one to four $R^d$ groups;
each $R^a$, $R^b$ and $R^c$ independently represents hydrogen, —$R^*$, —$C_{1-6}$ straight- or branched-chain alkyl, unsubstituted or substituted with one to four $R^d$ groups, or —$C_{3-7}$ cycloalkyl, unsubstituted or substituted with one to four $R^d$ groups;
or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to our $R^i$ groups;
or $R^b$ and $R^c$ taken together with any intervening atoms represent a 4–6 membered saturated ring optionally interrupted by one to three of O, S, $NR^a$, with $R^a$ as defined above, or —C(O)—, said ring being unsubstituted or substituted with one to four $R^i$ groups;
each $R^d$ independently represents halo; —CN; —$NO_2$; —$NR^e R^f$; —$OR^g$; —$SR^g$; —$CONR^e R^f$; —$COOR^g$; —$SOR^g$; —$SO_2 R^g$; —$SO_2 NR^e R^f$; —$NR^e SO_2 R^f$; —$COR^e$; —$NR^e\ COR^f$; —$OCOR^e$; —$OCONR^e R^f$; —$NR^e CONR^f R^g$; —$NR^e CO_2 R^h$; —$OCO_2 R^h$; —$C(NR^e)NR^f R^g$; —$NR^e C(NH)NR^f R^g$; —$NR^e C(NR^f) R^g$; —$R^*$ or —Q;
$R^e$, $R^f$ and $R^g$ represent hydrogen; —$R^*$; —$C_{1-6}$ straight- or branched-chain alkyl unsubstituted or substituted with one to four $R^i$ groups;
or $R^e$ and $R^f$ taken together with any intervening atoms represent a 4–6 membered saturated ring optionally interrupted by one to three of O, S, —C(O)— or $NR^g$ with $R^g$ as defined above, said ring being unsubstituted or substituted with one to four $R^i$ groups;
each $R^i$ independently represents halo; —CN; —$NO_2$; phenyl; —$NHSO_2 R^h$; —$OR^h$, —$SR^h$; —$N(R^h)_2$; —$N^+ (R^h)_3$; —$C(O)N(R^h)_2$; —$SO_2 N(R^h)_2$; heteroaryl; heteroarylium; —$CO_2 R^h$; —$C(O)R^h$; —$OCOR^h$; —$NHCOR^h$; guanidinyl; carbamimidoyl or ureido;
each $R^h$ independently represents hydrogen, a —$C_{1-6}$ straight or branched-chain alkyl group, a —$C_3$–$C_6$ cycloalkyl group or phenyl, or when two $R^h$ groups are present, said $R^h$ groups may be taken in combination and represent a 4–6 membered saturated ring, optionally interrupted by one or two of O, S, SO$_2$, —C(O)—, NH and NCH$_3$;

Q is selected from the group consisting of:

wherein:
a and b are 1, 2 or 3;
L$^-$ is a pharmaceutically acceptable counterion;
α represents O, S or NR$^s$;
β, δ, λ, μ and σ represent CR$^t$, N or N$^+$R$^s$, provided that no more than one of β, δ, λ, μ and σ is N$^+$R$^s$;
R* is selected from the group consisting of:

wherein:
d represents O, S or NR$^k$;
e, g, x, y and z represent CR$^m$, N or N$^+$R$^k$, provided that no more than one of e, g, x, y and z in any given structure represents N$^+$R$^k$;
R$^k$ represents hydrogen; —C$_{1-6}$ straight- or branched-chain alkyl, unsubstituted or substituted with one to four R$^i$ groups; or —(CH$_2$)$_n$Q where n=1, 2 or 3 and Q is as previously defined;
each R$^m$ independently represents a member selected from the group consisting of: hydrogen; halo; —CN; —NO$_2$; —NR"R$^o$; —OR"; —SR"; —CONR"R$^o$; —COOR$^h$; —SOR"; —SO$_2$R"; —SO$_2$NR"R$^o$; —NR"SO$_2$R$^o$; —COR"; —NR"COR$^o$; —OCOR"; —OCONR"R$^o$; —NR"CO$_2$R$^h$; —NR"CONR$^o$R$^h$; —OCO$_2$R$^h$; —CNR"NR$^o$R$^h$; —NR"CNHNR$^o$R$^h$; —NR"C(NR$^o$)R$^h$; —C$_{1-6}$ straight- or branched-chain alkyl, unsubstituted or substituted with one to four R$^i$ groups; —C$_{3-7}$ cycloalkyl, unsubstituted or substituted with one to four R$^i$ groups; and —(CH$_2$)$_n$Q where n and Q are as defined above;
R" and R$^o$ represent hydrogen, phenyl; —C$_{1-6}$ straight- or branched-chain chain alkyl unsubstituted or substituted with one to four R$^i$ groups;
each R$^s$ independently represents hydrogen; phenyl or —C$_{1-6}$ straight- or branched-chain alky, unsubstituted or substituted with one to four R$^i$ groups;
each R$^t$ independently represents hydrogen; halo; phenyl; —CN; —NO$_2$; —NR"R$^v$; —OR"; —SR"; —CONR"R$^v$; —COOR$^h$; —SOR"; —SO$_2$R"; —SO$_2$NR"R$^v$; —NR"SO$_2$R$^v$; —COR"; —NR"COR$^v$; —OCOR"; —OCONR"R$^v$; —NR"CO$_2$R$^v$; —NR"CONR$^v$R$^w$; —OCO$_2$R$^v$; —C$_{1-6}$ straight- or branched-chain alkyl, unsubstituted or substituted with one to four R$^i$ groups;

R" and R$^v$ represent hydrogen or —C$_{1-6}$ straight- or branched-chain alkyl, unsubstituted or substituted with one to four R$^i$ groups;
or R" and R$^v$ together with any intervening atoms represent a 4–6 membered saturated ring optionally interrupted by one or more of O, S, NR$^w$ or —C(O)—, said ring being unsubstituted or substituted with one to four R$^i$ groups;
each R$^w$ independently represents hydrogen; —C$_{1-6}$ straight- or branched-chain alkyl, unsubstituted or substituted with one to four R$^i$ groups; C$_{3-6}$ cycloalkyl optionally substituted with one to four R$^i$ groups; phenyl optionally substituted with one to four R$^i$ groups, or heteroaryl optionally substituted with 1–4 R$^i$ groups;
or R$^h$ and R$^w$ taken together with any intervening atoms represent a 5–6 membered saturated ring, optionally interrupted by one or two of O, S, SO$_2$, NH or NCH$_3$;
R$^x$ represents hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two C$_{1-3}$ straight- or branched-chain alkyl groups, said alkyl groups being unsubstituted or substituted with one to four R$^i$ groups;
R$^y$ and R$^z$ represent hydrogen; phenyl; —C$_{1-6}$ straight or branched chain alkyl, unsubstituted or substituted with one to four R$^i$ groups, and optionally interrupted by O, S, NR$^w$, N$^+$R$^h$R$^w$ or —C(O)—;
or R$^x$ and R$^y$ together with any intervening atoms represent a 4–6 membered saturated ring optionally interrupted by O, S, SO$_2$, NR$^w$, N$^+$R$^h$R$^w$ or —C(O)—, unsubstituted or substituted with 1–4 R$^i$ groups,
and when R$^x$ and R$^y$ together represent a 4–6 membered ring as defined above, R$^z$ is as defined above or R$^z$ represents an additional saturated 4–6 membered ring fused to the ring represented by R$^x$ and R$^y$ taken together, optionally interrupted by O, S, NR$^w$ or —C(O)—, said rings being unsubstituted or substituted with one to four R$^i$ groups;
and another antibiotic including β-lactams such as carbapenems.

2. A composition according to claim 1 wherein the compounds of structural formula I are represented by formula Ie:

or a pharmaceutically acceptable salt thereof, wherein:
R contains a positively charged moiety selected from the group consisting of: —R*, Q, and a C$_{1-6}$ straight or branched alkyl chain substituted with one R$^d$ group;
R$^d$ is independently selected —R* or Q;

Q is selected from the group consisting of:

and wherein L⁻, a and b are as originally defined, and R$^x$ represents a member selected from the group consisting of: hydrogen or a $C_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two $C_{1-3}$ straight- or branched-chain alkyl groups, said alkyl groups being unsubstituted or substituted with one to four R$^i$ groups;

R* is selected from:

wherein d represents NR$^k$; R$^k$ represents —$C_{1-6}$ straight or branched chain alkyl; and e, g, x and y represent CR$^m$ or N$^+$R$^k$, with R$^k$ as defined above and R$^m$ representing hydrogen.

3. A composition according to claim 1 wherein the compounds of formula I are:
(1S,5R,6S)-2-(5-(((carbamoylmethyl)-1,4-diazoniabicyclo[2.2.2]oct-1-yl)methyl)(1,8-naphthosultam)methyl)-6-[1(R)-hydroxyethyl]-1-methylcarbapen-2-em-3-carboxylate chloride;
(1S,5R,6S)-2-(5-(((3-hydroxyprop-1-yl)-1,4-diazoniabicyclo[2.2.2]oct-1-yl)methyl)(1,8-naphthosultam)methyl)-6-[1(R)-hydroxyethyl]-1-methylcarbapen-2-em-3-carboxylate chloride;
(1S,5R,6S)-2-(5-((1-methylimidazol-3-ium)methyl)(1,8-naphthosultam)methyl)-6-[1(R)-hydroxyethyl]-1-methylcarbapen-2-em-3-carboxylate;
(1S,5R,6S)-2-(5-(((2-(1-methylimidazol-3-ium)-ethyl)(1,8-naphthosultam)methyl)-6-[1(R)-hydroxyethyl]-1-methylcarbapen-2-em-3-carboxylate;
(1S,5R,6S)-2-(4-(((carbamoylmethyl)-1,4-diazoniabicyclo[2.2.2]oct-1-yl)methyl)(1,8-naphthosultam)methyl)-6-[1(R)-hydroxyethyl]-1-methylcarbapen-2-em-3-carboxylate chloride;
(1S,5R,6S)-2-(4-(2-(((carbamoylmethyl)-1,4-diazoniabicyclo[2.2.2]oct-1-yl)) -ethyl)(1,8-naphthosultam)methyl)-6-[1(R)-hydroxyethyl]-1-methylcarbapen-2-em-3-carboxylate chloride;
(1S,5R,6S)-2-(4-(2-(((3-hydroxyprop-1-yl)-1,4-diazoniabicyclo[2.2.2]oct-1-yl))-ethyl)(1,8-naphthosultam)methyl)-6-[1(R)-hydroxyethyl]-1-methylcarbapen-2-em-3-carboxylate chloride; or
(1S,5R,6S)-2-(4-(2-((1-methylimidazol-3-ium))-ethyl)(1,8-naphthosultam)methyl)-6-[1(R)-hydroxyethyl]-1-methylcarbapen-2-em-3-carboxylate.

4. A composition according to claim 3 wherein the compounds of formula I are:
(1S,5R,6S)-2-(5-(((carbamoylmethyl)-1,4-diazoniabicyclo[2.2.2]oct-1-yl)methyl)(1,8 -naphthosultam)methyl)-6-[1(R)-hydroxyethyl]-1-methylcarbapen-2-em-3-carboxylate chloride;
(1S,5R,6S)-2-(4-(((carbamoylmethyl)-1,4-diazoniabicyclo[2.2.2]oct-1-yl)methyl)(1,8-naphthosultam)methyl)-6-[1(R)-hydroxyethyl]-1-methylcarbapen-2-em-3-carboxylate chloride; or
(1S,5R,6S)-2-(4-(2-(((carbamoylmethyl)-1,4-diazoniabicyclo[2.2.2]oct-1-yl)) -ethyl)(1,8-naphthosultam)methyl)-6-[1(R)-hydroxyethyl]-1-methylcarbapen-2-em-3-carboxylate chloride.

5. A composition according to claim 1 wherein the other antibiotic is selected from the group consisting of imipenem and meropenem.

6. An antibiotic composition comprising a pharmaceuticallly acceptable carrier, a therapeutically effective amount of a 2-(naphthosultamyl)methyl-carbapenem selected from (1S,5R,6S)-2-(5-(((carbamoylmethyl)-1,4-diazoniabicyclo[2.2.2]oct-1-yl)methyl)(1,8-naphthosultam)methyl)-6-[1(R)-hydroxyethyl]-1-methylcarbapen-2-em-3-carboxylate chloride;
(1S,5R,6S)-2-(4-(((carbamoylmethyl)-1,4-diazoniabicyclo[2.2.2]oct-1-yl)methyl)(1,8-naphthosultam)methyl)-6-[1(R)-hydroxyethyl]-1-methylcarbapen-2-em-3-carboxylate chloride; and
(1S,5R,6S)-2-(4-(2-(((carbamoylmethyl)-1,4-diazoniabicyclo[2.2.2]oct-1-yl)) -ethyl)(1,8-naphthosultam)methyl)-6-[1(R)-hydroxyethyl]1-methylcarbapen-2-em-3-carboxylate chloride; and a therapeutically effective amount of another antibiotic selected from carbapenems.

7. A composition according to claim 6 wherein the 2-(naphthosultamyl)methyl-carbapenem is (1S,5R,6S)-2-(4-(2-(((carbamoylmethyl)-1,4-diazoniabicyclo[2.2.2]oct-1-yl))-ethyl)(1,8-naphthosultam)methyl)-6-[1(R)-hydroxyethyl]-1-methylcarbapen-2-em-3-carboxylate chloride; and the other antibiotic is selected from imipenem and meropenem.

8. A composition according to claim 1 wherein the carbapenem is imipenem, (4R,5S,6S)-3-[(3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid, or meropenem, from about 1 to about 100 mg/kg, and the 2-(naphthosultamyl)methyl-carbapenem is (1S,5R,6S)-2-(4-(2-(((carbamoylmethyl)-1,4-diazoniabicyclo[2.2.2]oct-1-yl))-ethyl)(1,8-naphthosultam)methyl)-6-[1(R) -hydroxyethyl]-1-methylcarbapen-2-em-3-carboxylate chloride, from about 0.1 to about 50 mg/kg.

9. A composition according to claim 8 wherein the amount of imipenem, (4R,5S,6S)-3-[(3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid, or meropenem is about 2 to about 50 mg/kg and the amount of (1S,5R,6S)-2-(4-(2-(((carbamoylmethyl)-1,4-diazoniabicyclo[2.2.2]oct-1-yl))-ethyl)(1,8-naphthosultam)methyl)-6-[1(R)-hydroxyethyl]-1-methylcarbapen-2-em-3-carboxylate chloride is about 0.5 to about 20 mg/kg.

10. An antibacterial composition comprising a pharmaceutically acceptable carrier, about 2 to about 50 mg/kg of imipenem, a pharmaceutically acceptable amount of cilastatin and about 0.5 to about 20 mg/kg of (1S,5R,6S)-2-(4-(2-(((carbamoylmethyl)-1,4-diazoniabicyclo-[2.2.2]oct-1-yl))-ethyl)(1,8-naphthosultam)methyl)-6-[1(R)-hydroxyethyl]-1-methylcarbapen-2-em-3-carboxylate chloride.

11. A composition according to claim 1 comprising 2-(naphthosultamyl)methyl-carbapenem antibacterial agents or ophthamologically acceptable salts thereof, in combination with a imipenem, (4R,5S,6S)-3-[(3S,5S)-5-(3-carboxyphenylcarbamoyl)pyrrolidin-3-ylthio]-6-(1R)-1-hydroxyethyl]-4-methyl-7-oxo-1-azabicyclo[3.2.0]hept-2-ene-2-carboxylic acid, or meropenem.

12. A method of treating or preventing a bacterial infection in a mammalian patient in need thereof, comprising administering to said patient an effective amount of a composition of claim 1.

13. A method of treating or preventing enterococcal or MRSA infections which comprises administering to a patient in need of such treatment of a unit dose of the composition of claim 1.

14. A method of treating or preventing enterococcal or MRSA infections which comprises administering to a patient in need of such treatment of a unit dose of the composition of claim 6.

15. A method of treating or preventing enterococcal or MRSA infections which comprises administering to a patient in need of such treatment of a unit dose of the composition of claim 10.

* * * * *